US007868627B2

(12) United States Patent
Turkovskyi

(10) Patent No.: US 7,868,627 B2
(45) Date of Patent: Jan. 11, 2011

(54) METHOD AND A DEVICE FOR MEASURING DIELECTRIC CHARACTERISTICS OF MATERIAL BODIES

(75) Inventor: Ivan I. Turkovskyi, St. Petersburg (RU)

(73) Assignee: Joint-Stock Company 'High Tech', St. Petersburg (RU)

( * ) Notice: Subject to any disclaimer, the term of this patent is extended or adjusted under 35 U.S.C. 154(b) by 0 days.

(21) Appl. No.: 12/537,771

(22) Filed: Aug. 7, 2009

(65) Prior Publication Data

US 2010/0001747 A1  Jan. 7, 2010

Related U.S. Application Data

(63) Continuation of application No. PCT/RU2008/000046, filed on Jan. 25, 2008.

(30) Foreign Application Priority Data

Feb. 14, 2007   (RU) ............................... 2007107047

(51) Int. Cl.
G01R 27/00 (2006.01)
G01R 31/12 (2006.01)
G01N 21/17 (2006.01)
(52) U.S. Cl. ...................... 324/642; 324/637; 324/638; 324/702
(58) Field of Classification Search ................ 324/702, 324/637, 638
See application file for complete search history.

(56) References Cited

U.S. PATENT DOCUMENTS 5,345,243 A   9/1994 Levis 6,100,703 A * 8/2000 Davidov et al. ............. 324/631
6,798,216 B2 * 9/2004 Jannsen et al. .............. 324/646

FOREIGN PATENT DOCUMENTS

| RU | 2078336 C1 | 4/1997 |
| RU | 2095812 C1 | 11/1997 |
| RU | 2098016 C1 | 12/1997 |
| SU | 1830491 A1 | 7/1993 |
| SU | 1817555 A1 | 8/1995 |
| UA | 62343 A | 12/2003 |
| WO | 2006/069721 A2 | 7/2006 |

OTHER PUBLICATIONS

International Search Report, mailed Jun. 11, 2008, from International Application No. PCT/RU2008/000046 filed Jan. 25, 2008.
English translation of International Preliminary Report on Patentability, dated Oct. 20, 2009, from International Application No. PCT/RU2008/000046 filed Jan. 25, 2008.
Hayashi, Y. et al., "Free water content and monitoring of healing processes of skin burns studied by microwave dielectric spectroscopy in vivo," Phys. Med. Biol. 50 (2005) 599-612.

* cited by examiner

*Primary Examiner*—Timothy J Dole
*Assistant Examiner*—John Zhu
(74) *Attorney, Agent, or Firm*—Houston Eliseeva, LLP

(57) ABSTRACT

A method and a device for measuring dielectric characteristics by generating a microwave signal, dividing the signal into reference and sounding signals, irradiating a body with the microwave signal, receiving the reflected, reference and total signals and in detecting said signals. The irradiation is carried out by a waveguide wave, the wave number of which in the free space filled with dielectric, is selected within a range from 1.0 to 1.07 the propagation number of the waveguide wave.

4 Claims, 1 Drawing Sheet

PATH OF REFLECTED RADIATION

METHOD AND A DEVICE FOR MEASURING DIELECTRIC CHARACTERISTICS OF MATERIAL BODIES

RELATED APPLICATIONS

This application is a Continuation of International Application No. PCT/RU2008/000046 filed Jan. 25, 2008, which claims priority to Russian Patent Application No. 2007107047 filed Feb. 14, 2007, both of which are incorporated herein by reference in their entirety.

FIELD OF THE INVENTION

The invention relates to biology, agriculture, the food industry, analytic chemistry, materials science, medicine, cosmetology, etc. The invention can be used for the measurement of the components of complex dielectric permittivity of objects and materials in the range of millimeter radiowaves and, in particular for the calculation of the parameters of the moisture content of objects and materials on the basis of the data of measured complex dielectric permittivity, as well as for the quantitative assessment of the structural organization of water in the composition of the materials investigated.

BACKGROUND OF THE INVENTION

Means for the determination of the dielectric permittivity of materials, based on the measurement of the reflection of electrical signals from the end of a dual-link coaxial cable upon its contact with the substance to be investigated are known (Yoshihito Hayashi et al., 2005, Phys. Med. Biol. 50, 599-612). However, due to the strong attenuation of the SHF signals in the coaxial (dual-link) cable at comparable wavelengths and cable radius, at frequencies above 10 GHz, performing measurements of complex dielectric permittivity becomes a very difficult technical problem.

In inventor's certificate SU No. 1830491, "Method of Determination of the Dielectric Parameters of an Object," the measurement of complex dielectric permittivity of an object is accomplished on the basis of the parameters of reflected radiation of a specimen placed in the measuring line. The method envisages the fabrication of a specimen of specified overall dimensions and form. Thus, the claims contain the phrases " . . . the specimen (material to be investigated) is made in the form of an insert, completely filling the cross-section of the transmission line, the coefficient . . . is measured . . . ." This approach is not suitable for the intravital measurement of biological tissues in vivo; a method permitting processing of the parameters of the signal reflected from an object of arbitrary form and dimensions, reflected from the boundary of the waveguide probe and the object being measured is necessary in this case.

Also, in inventor's certificate SU No. 1817555, "Method of Determination of the Dielectric Parameters of Materials," a method is implemented on the basis of the parameters of the wave in the probing channel "with the specimen to be investigated." A parameter of the specimen such as "1—specified length of the specimen to be investigated" is contained in the distinctive part and in the calculation formulas.

Patent RU No. 2 078 336, "Method of Monitoring the Properties of Materials on the Basis of Dielectric Loss Factor Variation and a Device for Implementing It," is also known, in which an alternative is proposed to the condenser method in the mid- to high-frequency region with the use of a mounted capacitance sensor in whose electrical field the material to be investigated is situated. A device implementing this method operates in "a wide range of frequencies (100 kHz-10 MHz) . . . ," i.e., in the radio range, maximum up to tens of megahertz. However, the circuit design of this device does not envisage operation in the range of tens of GHz, for which the device being applied for is proposed.

A method (Patent RF No. 2098016, priority of 30.01.97) of measurement of the dielectric parameters of bodies at a frequency of 30 GHz by means of a reflection SHF-dielectrometer with a single-link (circular) waveguide probe is also known.

The method includes the generation of an SHF signal, its division into a reference and a measuring signal, irradiation of the object to be measured by the latter, reception of the reflected signal modulated by a low-frequency signal, and then the determination of the physical parameter of the irradiated object from the reflected and the resultant signals. At the same time, the circuits of the measuring and the reference signals are equipped with waveguide transformers that provide the possibility of fine-tuning the path length, that in the process of measurement shift the phase of the measuring signal by $\pi$, and of the reference signal by $\pi/2$, radians.

A deficiency of said method and of the device implementing it is the necessity of observing the condition of good emitter matching (the waveguide probe) during irradiation of a material with specified reflective properties and dielectric permittivity close to those expected for the materials being tested. The absence of good emitter matching of the dielectric properties of the emitter and the materials being tested at the least reduces measurement accuracy, while a substantial mismatch of the dielectric properties of the emitter and the material being measured even in principle will prevent measurement of the dielectric parameters. This is explained by the following. The existence, at the open end-face of any waveguide, of several waves (modes) with different wave numbers and phase velocities is inevitable. The presence of several (and even more so, many) waves with different phase velocities prevents the obtaining of a stable interference pattern as the reflected and reference signals are superimposed. Thus, a single-mode waveguide is indispensable for unambiguous interpretation of the measurement results. However, single-mode radiation in an infinite waveguide is transformed into multimode radiation at the end-face of an open waveguide. The redistribution of energy to higher modes will be quite significant, because at the dielectric-filled (to ensure matching with the measurement medium) terminal segment of the waveguide probe, some of the local damping modes of the empty waveguide, having an imaginary wave number, will become propagating modes, i.e., having a real number, and the dielectric waveguide that is matched with respect to one mode will nonetheless be left mismatched with respect to other modes. Modes with several numbers n and m differing from zero will be propagating modes in a dielectric-filled waveguide with permittivity "$\in$," since the expression for the longitudinal wave number will be greater than zero ($\in \cdot k^2 - (m\pi/b)^2 - (n\pi/a)^2 > 0$) for several combinations of numbers n and m, whereas in the empty waveguide the condition ($k^2 - (m\pi/b)^2 - (n\pi/a)^2 > 0$) is observed only for m=0 and n=1. Here $\in$ is the relative dielectrical permittivity of the substance filling the waveguide probe; k is the wave number of the probe radiation in air (vacuum); a and b are the dimensions of the cross-section of the waveguide; and m and n are integers. In summary, multimode radiation emerges inevitably at the end-face of an open waveguide; however, after reflecting from the material being measured and passing further from the end-face to the detector in the empty waveguide duct, the reflected multimode radiation is converted nonetheless to single-mode. In a homogeneous waveguide, at a distance literally of one to two wavelengths from the boundary of the dielectric insert, only single-mode radiation is left as a result of the redistribution of the energy of the higher modes to the fundamental propagating mode. Nevertheless, local multimodality of the radiation, even only at the end-face, inevitably leads to a complex value of the impedance of the entire waveguide probe. A method of compensation of multimodality of the radiation at the end-face of a waveguide by means of waveguide transformers that achieve matching of impedances of a waveguide probe and the substance being measured is known (RF patent 2098016-prototype). In the device described in this patent, the multimodality of the reflected signal is not manifested only in the case of interaction with a load that is matched with the waveguide probe, but is not arbitrary. The obvious inconvenience of such a technical solution resides in the fact that, having achieved matching (equality) of the impedances of a waveguide and the substance being measured, it is further necessary to determine the impedances of the matched waveguide probe in the measuring line. In the end, measurement on such an instrument requires a set of standard specimens with known components of dielectric permittivity, and the measurement of the dielectric permittivity of an unknown material will correspond to the choice of a standard specimen that is maximally close by degree of matching (equality of the impedances securing the minimum SWR—standing-wave ratio). And the more accurate the measurement is required to be, the greater the number of standard specimens it will be necessary to have: the set of standard specimens must form a "matrix" of materials with fine gradation of their dielectric properties with respect to $\in'$ and $\in''$—the real and imaginary components of the complex dielectric permittivity. For example, if restricted to a "step" of unity with respect to $\in'$ and $\in''$, to measure the moisture content of material with an accuracy no worse than 1.5% (for such accuracy, a unit "step" with respect to $\in'$ and $\in''$ will at a minimum be sufficient), for an instrument at a frequency of 30 GHz a set of no fewer than 35·40=1400 standard specimens will be required; this makes the practical application of such a instrument difficult and significantly increases the cost of its production. The objective of the proposed solution is to increase the accuracy of measurements by achieving the independence of the process of measurement from matter of the matching of the impedances of the waveguide probe and the material being investigated.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

The interference principle of measurement of the modulus and argument of the complex reflection coefficient is implemented by means of a device whose block diagram is shown in FIG. 1. The position of the dielectric prism in the terminal section of the cavity of the waveguide probe and a wave undergoing internal reflection of the dielectric-air boundary are depicted schematically in FIG. 2. The position of the dielectric prism in the terminal section of the cavity of the waveguide probe and a wave passing through the dielectric-air boundary are depicted schematically in FIG. 3.

BRIEF SUMMARY OF THE INVENTION

Figure 1:
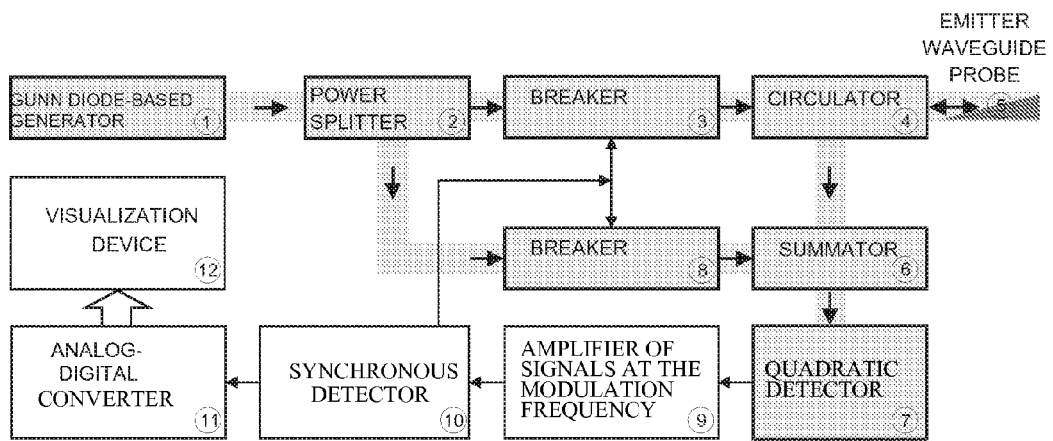

To accomplish the objective that has been set, in the proposed method of measurement of the dielectric characteristics of material bodies, which includes the generation of an EHF signal, its division into a reference and a probing signal, irradiation of the body by the EHF signal through contact of the waveguide probe with the material being investigated, reception of the reflected, reference, and resultant signals and their detection, a waveguide probe is used for irradiation, with an insert in the form of a prism of material with relative dielectrical permittivity $\in$, as well as a waveguide wave whose wave number in free space is selected within the limits of 1.0 to 1.07 times the longitudinal wave number of the waveguide wave, equal to $(\in k^2-(m\pi/b)^2-(n\pi/a)^2)$, where $\in k^2 >> (m\pi/b)^2+(n\pi/a)^2$, where $\in$ is the relative dielectrical permittivity of the material of the insert; a and b are the length and width of the cross-section of a rectangular waveguide (a<b): m and n are integers that are the orders of the propagating modes in the dielectric-filled waveguide; and k is the wave number of the millimeter radiation to be used in free space, equal to $k=2\pi v/c$, where v is frequency, and c is the speed of light in vacuum. The tuning of the difference of the phases of the reflected and the reference signals is carried out in the proposed method with a short-circuit waveguide through contact of the end-face of the waveguide probe with a polished metal mirror. The proposed method makes it possible to find an unambiguous correspondence between the measured complex reflection coefficient (its argument and modulus) and the dielectric parameters of the medium according to Fresnel's formulas, which describe the reflection of electromagnetic waves from the plane interface of two dielectrics.

In the proposed method the actual value of the impedance of the emitter is provided by excluding excitation of higher modes at the end-face of the waveguide probe. This condition can be attained if a waveguide wave is selected (used) that is maximally close in structure to the structure of a plane wave in unbounded space. For example, a wave whose wave number for free space—$(\in k^2)^{0.5}$—is no more than 7% greater than the longitudinal wave number h, at a measurement accuracy of the components of dielectric permittivity no worse than 1%:

$$h=(\in \cdot k^2-(m\pi/b)^2-(n\pi/a)^2)^{0.5}$$

i.e., the waveguide wave satisfies the condition:

$$\in \cdot k^2 >> (m\pi/b)^2-(n\pi/a)^2),$$

DETAILED DESCRIPTION OF THE PREFERRED EMBODIMENTS where a and b are the dimensions of the cross-section of the waveguide; $\in$ is the dielectrical permittivity of the medium filling the waveguide probe; k is the wave number for empty space; and m and n are the integers 0 and 1.

The phase of the complex coefficient of reflection from dielectrics with an actual impedance value in the given case will be independent of the dielectric properties, and in particular, from the absolute value of the impedance distribution of the material to be investigated.

The device contains a Gunn diode-based SHF generator 1 which is connected to power splitter 2; the probing signal from it arrives via series-connected first breaker 3 and circulator 4 at waveguide probe 5, is reflected from the material to be investigated, arrives at summator 6 via the same circulator 4, and then at quadratic detector 7. The reference signal arrives at summator 6 via the second breaker 8. The SHF signal arrives at quadratic detector 7 from summator 6, where it is detected. The signal, modulated at a low modulation frequency, arrives at analog-digital converter (ADC) 11 from quadratic detector 7 via amplifier 9, which amplifies signals at the modulation frequency, via synchronous detector 10, and then at visualization device 12 (for example, a computer monitor). The synchronous detector at the modulation frequency controls the opening and closing of the two breakers (p-i-n diodes). The path of the SHF signal in the waveguide is indicated by a double line with an arrow between the lines; and the direction of the low-frequency-modulated signal in the electric cable is indicated by a single arrow.

Waveguide probe 5 is filled with material in the form of a prism (FIG. 2 and FIG. 3) with dielectric permittivity $\in$.

The device operates as follows.

The SHF generator operates in continuous-wave mode; the time of a single measurement of the complex reflection coefficient is 0.1-100 msec, and consists of the following stages (FIG. 1).

1. First breaker 3 (p-i-n diode) is open, second breaker 8 is closed. Reflected signal $U_1$ arrives at quadratic detector 7.

2. Second breaker 8 (p-i-n diode) is open, first breaker 3 is closed. Reference signal $U_2$ arrives at quadratic detector 7.

3. Both breakers 3 and 8 are open; the result of interference of the reflected and the reference signals—the resultant signal $U_3$—arrives at quadratic detector 7.

The resultant signal, according to the cosine rule, is related to the reference and the reflected signals by the following equation:

$$U_3 = U_1 + U_2 - 2(U_1 U_2)^{0.5} \cdot \cos(\upsilon - \upsilon_0),$$

where $\upsilon$—is the argument of the complex reflection coefficient, $\upsilon_0$—is the calibration constant of the instrument.

Based on the cosine rule, the difference between the phases of the reference and the reflected signals can be found from the vector diagram of the three signals—the reflected, the reference, and the resultant:

$$(\upsilon - \upsilon_0) = \arccos\left[ U_1 + U_2 - U_3)/2 \cdot (U_1 \cdot U_2)^{0.5}\right]$$

The calibration of the amplitude and phase of the reflected signal is made with respect to the amplitude of the signal reflected from the short-circuit waveguide of the emitter (a metal mirror with fine alignment of the mirror surface toward the end-face of the dielectric-filled waveguide probe 5).

The amplitude of the signal reflected from the metal mirror is the normalization factor; the phase is the initial phase $\upsilon_0$.

The ratio of the amplitude of the reflected signal of the working measurement and the normalization factor is the modulus of the complex reflection coefficient.

The normalization factor is equal to the division ratio of the amplitudes of the probing and reference signals, and its value is selected close to unity.

The argument of the complex reflection coefficient is the difference of the phases of the working and calibration measurements.

Figure 2:
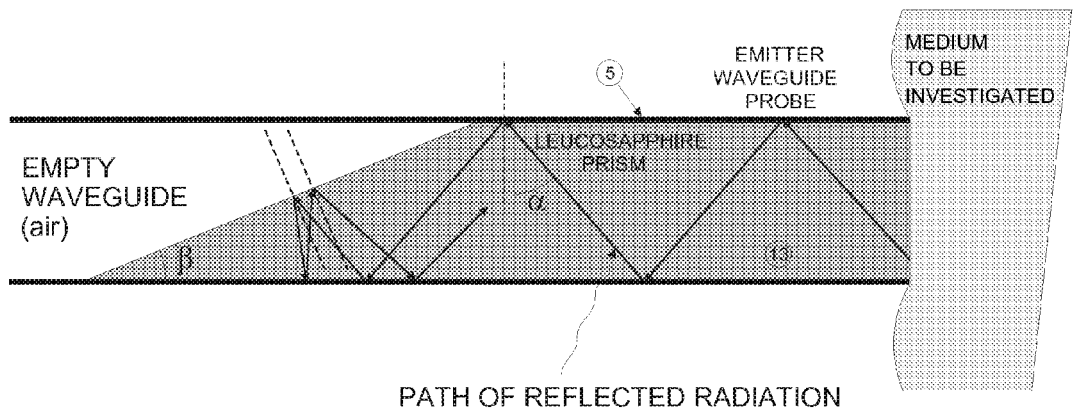
Figure 3:
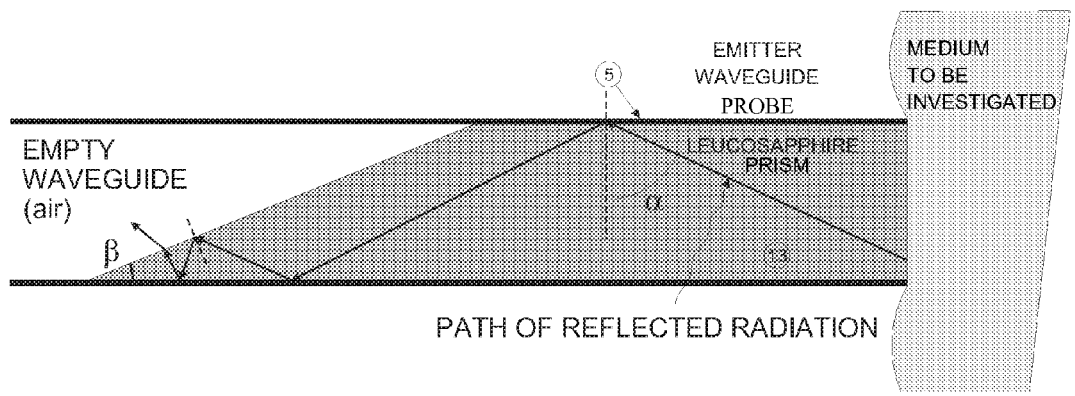

The emitter device (waveguide probe) 5 that is filled in the terminal segment with dielectric 13, for example, corundum, ceramic, diamond, leucosapphire, with dielectric permittivity $\in' \geq 10$ and $\in'' \sim 0$, is illustrated in FIG. 2. The reflected second harmonic $H_{01}$ mode passing through the prism face into the waveguide cavity is depicted in FIG. 3, while the modes undergoing complete reflection at the oblique prism face and, accordingly, not passing into the waveguide cavity, are collectively depicted in FIG. 2. The filling of the dielectric is made in the form of a matching oblique angle prism, in which the fundamental propagating $H_{01}$ mode satisfies the condition $\in \cdot k^2 \gg (m\pi/b)^2 + (n\pi/a)^2$, and the other modes of the reflected radiation do not pass into the empty waveguide. The filtration of the higher modes is achieved by segments of smooth tapering of the waveguide tract (waveguide filters) or by an additional condition on the angle of inclination of the face of the oblique angle prism 13 to the axis of the waveguide. Thus, the general condition of the passage of the reflected waveguide radiation from the dielectric prism into the waveguide tract relating the dielectric permittivity of the substance of the prism, the angle of inclination of the face of the prism to the axis of the waveguide, the cross-section dimensions of the waveguide, the value of the wave vector, and the orders of the reflected mode passing into the waveguide, are linked by the expression:

$$\arcsin([\in \cdot k^2 - (m\pi/b)^2 - (n\pi/a)^2]^{0.5}/[\in \cdot k^2]^{0.5}) - (2g+1) \cdot \in < \arcsin(1/\sqrt{\in})$$

Here $\in$ is the relative dielectrical permittivity of the material of the prism insert; a and b are the length and width of the cross-section of a rectangular waveguide; m and n are integers that are the orders of the propagating modes of the dielectric-filled waveguide; g is an integer: 1, 2, 3 . . . ; k is the wave number of the millimeter radiation to be used for free space ($k = 2\pi\upsilon/c$, where $\upsilon$ is frequency, and c is the speed of light in vacuum); and $\beta$ is the angle of inclination of the face of the prism to the axis of the waveguide.

A schematic of the passage of the reflected second harmonic $H_{01}$ wave (that satisfies the condition $\in \cdot k^2 \gg (m\pi/b)^2 + (n\pi/a)^2$) of the radiation of the Gunn diode-based SHF generator from a leucosapphire oblique angle prism at the end-face of the waveguide probe into the empty waveguide is given in FIG. 3. All other propagating modes at the interface of the inclined face of the prism and the empty waveguide have such angles of incidence that they experience internal reflection and do not pass into the waveguide tract (FIG. 2). The probing radiation is not represented in order to avoid overloading the figure. Since for the reflected mode passing into the waveguide the angle between the direction of the propagation of the reflected mode and the traverse of the waveguide, "$\alpha$," is equal to $\arcsin(h/\sqrt{\in} \cdot k)$, and thus close to 90°, the $H_{01}$ wave is propagated essentially horizontally from the medium being investigated before reflection from the inclined plane of the prism, like a plane transverse wave in free space.

Thus, by contrast with the prototype, in which tuning of the phase of the reflected and the reference signals by waveguide transformers, providing complete matching of the impedances of the waveguide probe and the specimen to be measured, is necessary to achieve the measurement of the components of complex dielectric permittivity of each new material, the impedance (the ratio of the tangential components E and H of the fields of the waveguide wave) of the waveguide probe we are proposing has in practice exclusively either a real or an imaginary value. If the absolute value of the impedance of the waveguide is greater than the load impedance, the waveguide probe has an imaginary impedance; if it is less, it has a real one.

In consequence of an exclusively real or imaginary value of the impedance of the waveguide, higher modes do not arise during contact of the waveguide probe even with a substantially mismatched load at the "waveguide—substance to be investigated" boundary, while the waveguide wave of the probing and the reflected radiation is close in structure to a plane wave in infinite space, and the Fresnel formulas describing the reflection and refraction of plane electromagnetic waves at the plane interface of two dielectrics are applicable for finding the relationship between the dielectric parameters ($\in'$ and $\in''$) of the medium and the amplitude and the argument of the measured complex coefficient of reflection. In summary, fine-tuning of the phase of the reflected and the reference signals is not required for each measurement of the dielectric parameters of each new substance, and phase tuning (calibration of the instrument) is done with a stable generator only once (for example, once a day or a month) by means of a short-circuit waveguide—for example, on a polished metal mirror.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for measuring dielectric characteristics of materials, comprising:
   generating an extremely high frequency (EHF) signal,
   dividing the EHF signal into a reference signal and a probe signal,
   contacting the material with a rectangular waveguide comprising a prism-shaped dielectric insert, wherein the insert is in contact with the material,
   irradiating the material with the EHF signal through the waveguide,
   receiving a reflected signal, a reference signal, and a combined signal, and
   detecting the reflected signal, the reference signal, and the combined signal,
   wherein the ratio of the wave number of the EHF signal in dielectric-filled free space to the longitudinal wave number of the EHF signal in the waveguide is $(\in \cdot k^2)^{0.5}/(\in \cdot k^2 - (\pi/a)^2)^{0.5}$ and is between 1 and 1.07,
   where $\in$ is a relative dielectric permittivity of the insert;
   where a is the smaller dimension of the rectangular cross-section of the waveguide; and
   where k is a wave number of the EHF signal for empty free space equal to $k=2\pi v/c$, where v is the radiation frequency, and c is the speed of light in vacuum.

2. The method according, to claim 1, further comprising tuning of phase difference between the reflected and the reference signals using a short-circuit waveguide.

3. The method according to claim 2, wherein the tuning of the phase difference between the reflected and the reference signals comprises contacting an end-face of the waveguide with a polished metal mirror.

4. A device for measuring dielectric characteristics of materials, comprising:
   an extremely high frequency (EHF) generator comprising a first output,
   a power splitter comprising an input, a first output, and a second output,
   a first breaker comprising an output, a first input, and a second input,
   a second breaker comprising an output, a first input, and a second input,
   a circulator comprising an input, a first output, and a second output,
   a rectangular waveguide probe,
   a dielectric prism mounted within a cavity of a terminal section of the waveguide probe;
   a summator comprising an output, a first input, and a second input,
   a quadratic detector comprising an input and an output,
   an amplifier for signals at a modulation frequency,
   a synchronous detector comprising a first output,
   an analog-to-digital converter (ADC), and
   a visualization device,
   wherein the first output of the EHF generator is connected with the input of the power splitter,
   wherein the first output of the power splitter is connected with the first input of the first breaker,
   wherein the second output of the power splitter is connected with the first input of the second breaker,
   wherein the second input of the first breaker is connected with the first output of the synchronous detector,
   wherein the second input of the second breaker is connected with the first output of the synchronous detector,
   wherein the output of the first breaker is connected with the input of the circulator,
   wherein the first output of the circulator is connected with the waveguide probe,
   wherein the second output of the circulator is connected with the first input of the summator,
   wherein the second input of the summator is connected with the output of the second breaker,
   wherein the output of the summator is connected with the input of the quadratic detector,
   wherein the output of the summator is serially connected with the amplifier, the synchronous detector, the ADC, and the visualization device,
   wherein, for at least one positive integer g, the following conditions linking the relative dielectric permittivity of the material of the prism, an inclination angle of a face of the prism to an axis of the waveguide probe, a cross-section of the waveguide probe, and the wave number hold: $0 < \arc\sin([\in \cdot k^2 - (m\pi/b)^2 - (n\pi/a)^2]^{0.5}/[\in \cdot k^2]^{0.5}) - (2g+1)\cdot\beta < \arc\sin(1/\sqrt{\in})$,
   where $\in$ is the relative dielectric permittivity of the material of the prism,
   where a and b are a length and a width of the cross-section of the waveguide probe,
   where $\beta$ is the inclination angle of the face of the dielectric prism to the axis of the waveguide probe,
   where m and n are integers and are orders of propagating modes of the dielectric-filled waveguide,
   where g is an integer greater than zero,
   where k is a wave number of EHF radiation generated for empty free space equal to $k=2\pi v/c$, where v is the radiation frequency, and c is the speed of light in vacuum.

* * * * *